(12) United States Patent
Chari et al.

(10) Patent No.: US 6,630,579 B2
(45) Date of Patent: Oct. 7, 2003

(54) CYTOTOXIC AGENTS COMPRISING MODIFIED DOXORUBICINS AND DAUNORUBICINS AND THEIR THERAPEUTIC USE

(75) Inventors: Ravi V. J. Chari, Newton, MA (US); Walter A. Blättler, Brookline, MA (US)

(73) Assignee: Immunogen Inc., Cambridge, MA (US)

( * ) Notice: Subject to any disclaimer, the term of this patent is extended or adjusted under 35 U.S.C. 154(b) by 194 days.

(21) Appl. No.: 09/740,991

(22) Filed: Dec. 21, 2000

(65) Prior Publication Data

US 2001/0036923 A1 Nov. 1, 2001

Related U.S. Application Data

(60) Provisional application No. 60/173,497, filed on Dec. 29, 1999.

(51) Int. Cl.[7] .......................... C07H 15/24; A61K 31/70
(52) U.S. Cl. ...................... 536/6.4; 514/34; 424/179.1; 424/181.1
(58) Field of Search ..................... 536/6.4; 514/34; 424/179.1, 181.1

(56) References Cited

U.S. PATENT DOCUMENTS

| | | | |
|---|---|---|---|
| 4,464,529 A | * | 8/1984 | Mosher et al. ............... 536/6.4 |
| 4,672,057 A | | 6/1987 | Bargiotti et al. |
| 5,304,687 A | | 4/1994 | Bargiotti et al. |
| 5,843,903 A | | 12/1998 | Schally et al. |

OTHER PUBLICATIONS

Matthews et al., Regulatory Toxicology and Pharmacology, vol. 28(3), pp. 242–264; 1998 (Abstract provided).*
Mazzini et al., Journal of the Chemical Society, (9), pp. 1983–1992; 1998 (abstract provided).*
Ripamonti et al., Investigational New Drugs, col. 14(2), pp. 139–1944; 1996 (abstract provided).*
Cancer Research 50, 6600–6607, Oct. 15, 1990; Evaluation in Vitro of Adriamycin Immunoconjugates Synthesized Using an Acid–sensitive Hydrazone Linker; Robert S. Greenfield, et al.
Cancer Research 50, 6608–6614, Oct. 15, 1990; Antitumor Activity of Adriamycin (Hydrazone–linked) Immunoconjugates Compared with Free Adriamycin and Specificity of Tumor Cell Killing; Gary R. Brawlawsky, et al.
Bioconjugate Chem. 1990 1,325–330; Antibody Conjugates with Morpholindoxorubicin and Acid–Cleavable Linker; Barbara M. Mueller, et al.
Journal of Medicinal Chemistry, 1984 vol. 27, No. 5; pp. 638–645; Intensely Potent Morpholinyl Anthracyclines; Edward M. Acton, et al.
J. Med. Chem. 1986, 29 2074–2079; N–(Cyanomethyl)— and N–(2–Methoxyl–1–cyanoethyl)anthracyclines and Related Carboxyl Derivatives; Edward M. Acton et al.
J. Med. Chem. 1986, 29 1225–1230, New Cyanomorpholinyl Byproduct of Doxorubicin Reductive Alkylation; Edward M. Acton, et al.
Journal of Clinical Onocology, vol. 17, No. 2 (Feb.) 1999 pp 478–484); Randomized Phase II Study of BR96–Doxorubicin Conjugate in Patients with Metastatic Breast Cancer; Anthony W. Tolcher, et al.
Pro. Natl. Acad. Sci, USA; vol. 93, pp. 2564–2469, Mar. 1996 Medical Sciences; High yield conversion of doxorubicin to 2–pyrrolinodoxorubicin, an analog 500–1000 times more potent: Structure–activity relationship of daunosamine–modified derivatives of doxorubicin; Attila Nagy, et al.

* cited by examiner

Primary Examiner—James O. Wilson
Assistant Examiner—Howard V. Owens, Jr.
(74) Attorney, Agent, or Firm—Sughrue Mion, PLLC

(57) ABSTRACT

A cytotoxic agent comprising one or more modified doxorubicins/daunorubicin linked to a cell binding agent. A therapeutic composition for killing selected cell populations comprising: (A) a cytotoxic amount of one or more modified doxorubicins/daunorubicins covalently bonded to a cell binding agent through a linking group, and (B) a pharmaceutically acceptable carrier. A method for killing selected cell populations comprising contacting target cells or tissue containing target cells with an effective amount of a cytotoxic agent comprising one or more modified doxorubicins/daunorubicins linked to a cell binding agent. Novel sulfur-containing modified doxorubicins/daunorubicins.

16 Claims, 3 Drawing Sheets

1. X = H: Morpholino Daunorubicin
2. X = OH: Morpholino Doxorubicin

3a: X = H
3b: X = OH

4a: X = H, R = Me
4b: X = OH, R = Me

5

6

X = H: Daunorubicin Compounds
X = OH: Doxorubicin Comounds

| Y | R | R' |
|---|---|---|
| O or $NR_2$ | H or alkyl | $-OCH_2CH_2CH(Me)SH$ |
| O or $NR_2$ | H or alkyl | $-OCH_2CH_2CH(Me)SSZ$ |
| O or $NR_2$ | $-CH_2SH$ or $-CH_2CH(Me)SH$ | -H or $-OR_1$ |
| O or $NR_2$ | $-CH_2SSZ$ or $-CH_2CH(Me)SSZ$ | -H or $-OR_1$ |

CYTOTOXIC AGENTS COMPRISING MODIFIED DOXORUBICINS AND DAUNORUBICINS AND THEIR THERAPEUTIC USE

This application claims the benefit of provisional application 60/173,497 filed Dec. 29, 1999.

FIELD OF THE INVENTION

The present invention relates to novel cytotoxic agents and their therapeutic use. More specifically, the invention relates to novel cytotoxic agents comprising modified doxorubicins/daunorubicins and their therapeutic use. These novel cytotoxic agents have therapeutic use as a result of delivering the modified doxorubicins/daunorubicins to a specific cell population in a targeted fashion by chemically linking the doxorubicin/daunorubicin to a cell binding agent.

BACKGROUND OF THE INVENTION

Many reports have appeared on the attempted specific targeting of tumor cells with monoclonal antibody-drug conjugates (Sela et al, in *Immunoconjugates* 189–216 (C. Vogel, ed. 1987); Ghose et al, in *Targeted Drugs* 1–22 (E. Goldberg, ed. 1983); Diener et al, in *Antibody mediated delivery systems* 1–23 (J. Rodwell, ed. 1988); Pietersz et al, in *Antibody mediated delivery systems* 25–53 (J. Rodwell, ed. 1988); Bumol et al, in *Antibody mediated delivery systems* 55–79 (J. Rodwell, ed. 1988). Cytotoxic drugs such as methotrexate, daunorubicin, doxorubicin, vincristine, vinblastine, melphalan, mitomycin C, and chlorambucil have been conjugated to a variety of murine monoclonal antibodies. In some cases, the drug molecules were linked to the antibody molecules through an intermediary carrier molecule such as serum albumin (Garnett et al, 46 *Cancer Res.* 2407–2412 (1986); Ohkawa et al, 23 *Cancer Immunol Immunother.* 81–86 (1986); Endo et al, 47 *Cancer Res.* 1076–1080 (1980)), dextran (Hurwitz et al, 2 *Appl. Biochem.* 25–35 (1980); Manabi et al, 34 *Biochem. Pharmacol.* 289–291 (1985); Dillman et al, 46 *Cancer Res.* 4886–4891 (1986); Shoval et al, 85 *Proc. Natl. Acad. Sci.* 8276–8280 (1988)), or polyglutamic acid (Tsukada et al, 73 *J. Natl. Canc. Inst.* 721–729 (1984); Kato et al, 27 *J. Med. Chem.* 1602–1607 (1984); Tsukada et al, 52 *Br. J. Cancer* 111–116 (1985)).

An array of linker technologies has been employed for the preparation of such immunoconjugates and both cleavable and non-cleavable linkers have been investigated. In most cases, the full cytotoxic potential of the drugs could only be observed, however, if the drug molecules could be released from the conjugates in unmodified form at the target site.

One of the cleavable linkers that has been employed for the preparation of antibody-drug conjugates is an acid-labile linker based on cis-aconitic acid that takes advantage of the acidic environment of different intracellular compartments such as the endosomes encountered during receptor mediated endocytosis and the lysosomes. Shen and Ryser introduced this method for the preparation of conjugates of daunorubicin with macromolecular carriers (102 *Biochem. Biophys. Res. Commun.* 1048–1054 (1981)). Yang and Reisfeld used the same technique to conjugate daunorubicin to an anti-melanoma antibody (80 *J. Natl. Canc. Inst.* 1154–1159 (1988)). Dillman et al also used an acid-labile linker in a similar fashion to prepare conjugates of daunorubicin with an anti-T cell antibody (48 *Cancer Res.* 6097–6102 (1988)).

An alternative approach, explored by Trouet et al, involved linking daunorubicin to an antibody via a peptide spacer arm (79 *Proc. Natl. Acad. Sci.* 626–629 (1982)). This was done under the premise that free drug could be released from such a conjugate by the action of lysosomal peptidases.

In vitro cytotoxicity tests, however, have revealed that antibody-drug conjugates rarely achieved the same cytotoxic potency as the free, unconjugated drugs. This suggested that mechanisms by which drug molecules are released from the antibodies are very inefficient. In the area of immunotoxins, conjugates formed via disulfide bridges between monoclonal antibodies and catalytically active protein toxins were shown to be more cytotoxic than conjugates containing other linkers. (See, Lambert et al, 260 *J. Biol. Chem.* 12035–12041 (1985); Lambert et al, in *Immunotoxins* 175–209 (A. Frankel, ed. 1988); Ghetie et al, 48 *Cancer Res.* 2610–2617 (1988)). This was attributed to the high intracellular concentration of glutathione contributing to the efficient cleavage of the disulfide bond between an antibody molecule and a toxin. Despite this, there are only a few reported examples of the use of disulfide bridges for the preparation of conjugates between drugs and macromolecules. Shen et al (260 *J. Biol. Chem.* 10905–10908 (1985)) described the conversion of methotrexate into a mercaptoethylamide derivative followed by conjugation with poly-D-lysine via a disulfide bond. Another report described the preparation of a conjugate of the trisulfide-containing toxic drug calicheamicin with an antibody (Hinman et al, 53 *Cancer Res.* 3336–3342 (1993)).

One reason for the lack of disulfide linked antibody-drug conjugates is the unavailability of cytotoxic drugs possessing a sulfur atom-containing moiety that can be readily used to link the drug to an antibody via a disulfide bridge. Furthermore, chemical modification of existing drugs is difficult without diminishing their cytotoxic potential.

Another major drawback with existing antibody-drug conjugates is their inability to deliver a sufficient concentration of drug to the target site because of the limited number of targeted antigens and the relatively moderate cytotoxicity of cancerostatic drugs like methotrexate, daunorubicin, doxorubicin and vincristine. In order to achieve significant cytotoxicity, linkage of a large number of drug molecules either directly to the antibody or through a polymeric carrier molecule becomes necessary. However such heavily modified antibodies often display impaired binding to the target antigen and fast in vivo clearance from the blood stream.

In spite of the above described difficulties, useful cytotoxic agents comprising cell binding moieties and the group of cytotoxic drugs known as maytansinoids have been reported (U.S. Pat. Nos. 5,208,020; 5,416,064; and R. V. J. Chari, 31 *Advanced Drug Delivery Reviews* 89–104 (1998)). Similarly, useful cytotoxic agents comprising cell binding moieties and analogues and derivatives of the potent antitumor antibiotic CC-1065 have also been reported (U.S. Pat. Nos. 5,475,092 and 5,585,499, both of which are expressly incorporated herein by reference).

Doxorubicin (Adriamycin) and daunorubicin (Daunomycin) are cytotoxic natural products that are widely used in the treatment of cancer. These compounds belong to the family of compounds called anthracyclines. Anthracyclines are DNA interacting agents that intercalate into the DNA and interfere with its template function causing cell death. While doxorubicin and daunorubicin are useful agents in the treatment of cancer, their anti-tumor activity is limited because of their non-specific toxicity towards normal cells.

Further, compounds like doxorubicin and daunorubicin themselves are not sufficiently potent to be used in conjugates of cell binding agents. Several attempts to link these compounds to antibodies have resulted in conjugates with low potency and poor target-selectivity (R. S. Greenfield et al, 50 *Cancer Res.* 6600–6607 (1990); R. S. Greenfield et al, 50 *Cancer Res.* 6608–6614 (1990); R. V. J. Chari, 31 *Advanced Drug Delivery Revs.* 89–104 (1998)). Thus, these conjugates have proven ineffective in human clinical trials (A. W. Tolcher et al, 17 *J. Clin. Oncol.* 478–484 (1999)). A few morpholino analogs with greater potency than either daunorubicin or doxorubicin have been described (E. M. Acton et al, 27 *J. Med. Chem.* 638–645 (1984); E. M. Acton et al, 29 *J. Med. Chem.*, 1225–1230 (1985); E. M. Acton et al, 29 *J. Med. Chem.* 2074–2079 (1986); U.S. Pat. Nos. 4,464,529, 4,672,057, 5,304,687(FIG. 1); and recently, a pyrrolinodoxorubicin ((5) in FIG. 1) has been described (A. Nagy et al, 93 Proc. Natl. Acad Sci., 2464–2469 (1996); U.S. Pat. No. 5,843,903). However, these compounds lack a functionality that allows linkage via a cleavable bond to cell binding agents. Also, one attempt to link morpholinodoxorubicin to an antibody via an acid-labile linker led to an unstable conjugate that was inactive (B. M Mueller et al, 1 *BioConjugate Chem.* 325–330 (1990)).

Accordingly, a method of treating diseases with doxorubicins/daunorubicins wherein their side effects are reduced without compromising their cytotoxicity is greatly needed.

SUMMARY OF THE INVENTION

One object of the present invention is to provide modified doxorubicins/daunorubicins that are highly toxic and that can still be effectively used in the treatment of many diseases.

Another object of the present invention is to provide novel modified doxorubicins/daunorubicins.

These and other objects have been achieved by providing a cytotoxic agent comprising one or more modified doxorubicins or daunorubicins linked to a cell binding agent.

In a second embodiment, the present invention provides a therapeutic composition comprising:

(A) a therapeutically effective amount of one or more modified doxorubicins or daunorubicins linked to a cell binding agent, and (B) a pharmaceutically acceptable carrier.

In a third embodiment, the present invention provides a method of killing selected cell populations comprising contacting target cells or tissue containing target cells with an effective amount of a cytotoxic agent comprising one or more modified doxorubicins or daunorubicins linked to a cell binding agent.

In a fourth embodiment, the present invention provides modified doxorubicins or daunorubicins comprising a linking group capable of linking said modified doxorubicins or daunorubicins to a chemical moiety.

DETAILED DESCRIPTION OF THE INVENTION

Figure 1:
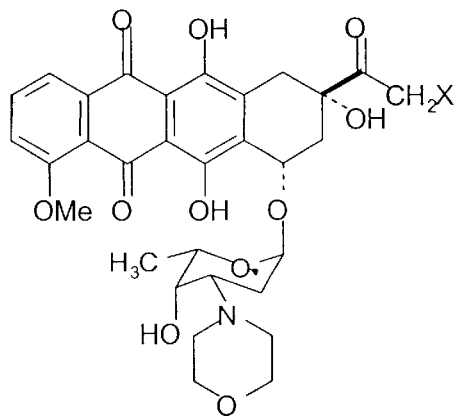
FIG. 1 shows the structure of various potent doxorubicin and daunorubicin analogs (E. M. Acton et al (1984, 1985, and 1986), supra).
Figure 1:
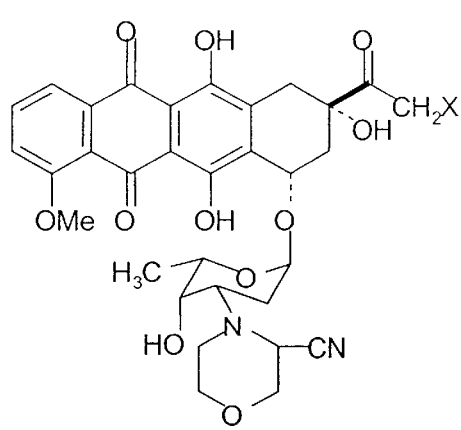
Figure 1:
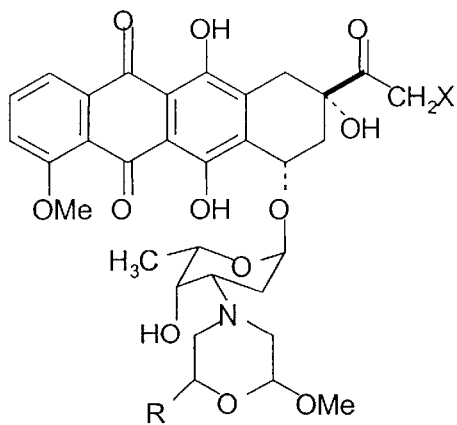
Figure 1:
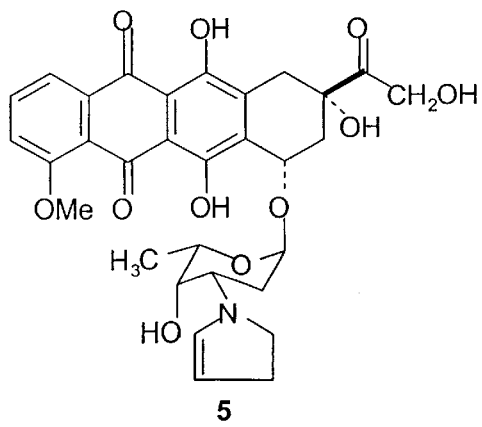

This invention is based on the synthesis of novel modified doxorubicins/daunorubicins that display enhanced cytotoxicity and that can be effectively linked to cell binding agents. The art reveals that it is extremely difficult to modify existing drugs without diminishing their cytotoxic potential. However, it has previously been shown that highly cytotoxic drugs can be modified in a way that leads to new drugs that have equivalent or greater potency than the parent drug. In addition, these highly cytotoxic drugs can be linked to cell binding agents using a cleavable link, such as a disulfide bond, ensuring the release of fully active drug inside the cell. Such conjugates are cytotoxic in an antigen specific manner (R. V. J. Chari et al, 52 *Cancer Res.* 127–131 (1992); U.S. Pat. Nos. 5,475,092; and 5,416,064). The disclosed invention applies this technology to doxorubicins and daunorubicins, which are modified with chemical moieties, and especially ones containing thiol or disulfide groups, to which appropriate cell binding agents can be linked. As a result, the disclosed novel modified doxorubicins/daunorubicins preserve and in some cases could even enhance the cytotoxic potency of known doxorubicins and daunorubicins. The cell binding agent-doxorubicin/daunorubicin complexes permit the full measure of the cytotoxic action of the doxorubicins/daunorubicins to be applied in a targeted fashion against unwanted cells only, therefore, avoiding side effects due to damage to non-targeted healthy cells. This invention permits the doxorubicins/daunorubicins to be target site-directed and still be effective. Thus the invention provides useful agents for the elimination of diseased or abnormal cells that are to be killed or lysed, such as tumor cells (particularly solid tumor cells), virus infected cells, microorganism infected cells, parasite infected cells, autoimmune cells (cells that produce autoantibodies), activated cells (those involved in graft rejection or graft vs. host disease), or any other type of diseased or abnormal cells, while exhibiting a minimum of side effects.

The cytotoxic agent according to the present invention comprises one or more modified doxorubicins/daunorubicins linked to a cell binding agent via a linking group. The linking group is part of a chemical moiety that is covalently bound to a modified doxorubicin/daunorubicin through conventional methods. While the drug can be linked to cell binding agents via cleavable bonds such as acid-labile, esterase-labile and peptidase-labile bonds, the preferred mode of linkage is via disulfide bonds.

The modified doxorubicins/daunorubicins useful in the present invention have the formula (I) shown below:

The modified doxorubicins/daunorubicins useful in the present invention have the formula (I) shown below:

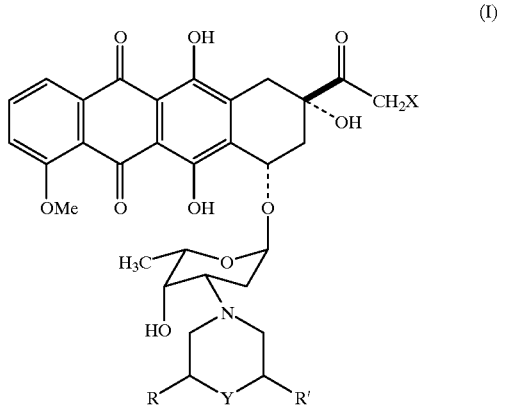

wherein,

X is H or OH;

Y is O or $NR_2$, wherein $R_2$ is linear or branched alkyl having 1 to 5 carbon atoms;

R is a linking group, H, or linear or branched alkyl having 1 to 5 carbon atoms; and R' is a linking group, H, or —$OR_1$, wherein $R_1$ is linear or branched alkyl having 1to 5 carbon atoms;

provided R and R' are not linking groups at the same time.

Examples of the linear or branched alkyl having 1 to 5 carbon atoms, represented by R, $R_1$, and $R_2$, include methyl, ethyl, n-propyl, isopropyl, n-butyl, isobutyl, sec.-butyl, tert.-butyl, and pentyl, in any of its eight isomeric arrangements.

$R_1$ and $R_2$ preferably are methyl.

Suitable linking groups are well known in the art and include disulfide groups, thioether groups, acid labile groups, photolabile groups, peptidase labile groups and esterase labile groups. Preferred are thioether groups and disulfide groups. The preferred positions for introduction of a thiol or disulfide group are at R and R'.

When the linking group is a thiol- or disulfide-containing group, the side chain carrying the thiol or disulfide group can be linear or branched, aromatic or heterocyclic. One of ordinary skill in the art can readily identify suitable side chains. Specific examples of the thiol- or disulfide-containing substituents include —$(CH_2)_nSZ$, —$O(CH_2)_nSZ$, —$(CH_2)_nCH(CH_3)SZ$, —$O(CH_2)_nCH(CH_3)SZ$, —$(CH_2)_nC(CH_3)_2SZ$, or —$O(CH_2)_nC(CH_3)_2SZ$, wherein Z is H or $SR_3$, wherein $R_3$ is linear, branched, or cyclic alkyl having from 1 to 10 carbon atoms, or simple or substituted aryl having from 1 to 10 carbon atoms, or heterocyclic having from 1 to 10 carbon atoms, and n is an integer of 1 to 10.

Examples of linear alkyls include methyl, ethyl, propyl, butyl, pentyl and hexyl.

Examples of branched alkyls include isopropyl, isobutyl, sec.-butyl, tert.-butyl, isopentyl and 1-ethyl-propyl.

Examples of cyclic alkyls include cyclopropyl, cyclobutyl, cyclopentyl and cyclohexyl.

Examples of simple aryls include phenyl and naphthyl.

Examples of substituted aryls include aryls such as those described above substituted with alkyl groups, with halogens, such as Cl, Br, F, nitro groups, amino groups, sulfonic acid groups, carboxylic acid groups, hydroxy groups and alkoxy groups.

Examples of heterocyclics are compounds wherein the heteroatoms are selected from O, N and S, and include pyrrollyl, pyridyl, furyl and thiophene.

Figure 2:
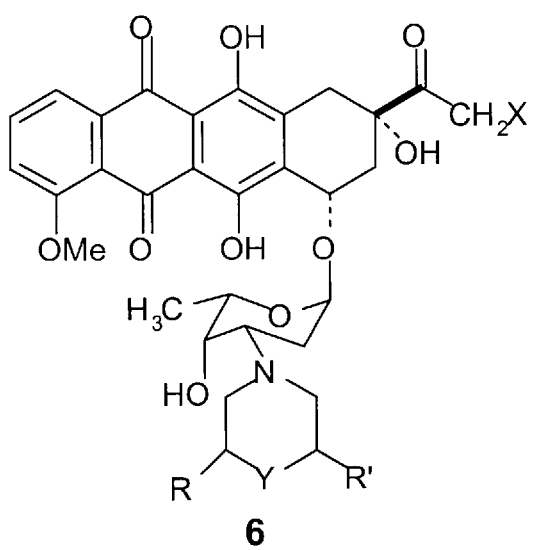
FIG. 2 is a chemical formula that represents structures of some of the disulfide-containing doxorubicins/daunorubicins according to the present invention. The substituents $R_1$, $R_2$ and Z are as defined herein.

The modified doxorubicins/daunorubicins of the present invention, which have a thiol- or disulfide-containing substituent are in themselves novel. Examples of some preferred thiol- or disulfide-containing doxorubicins and daunorubicins according to the present invention are shown in FIG. 2.

Figure 3:
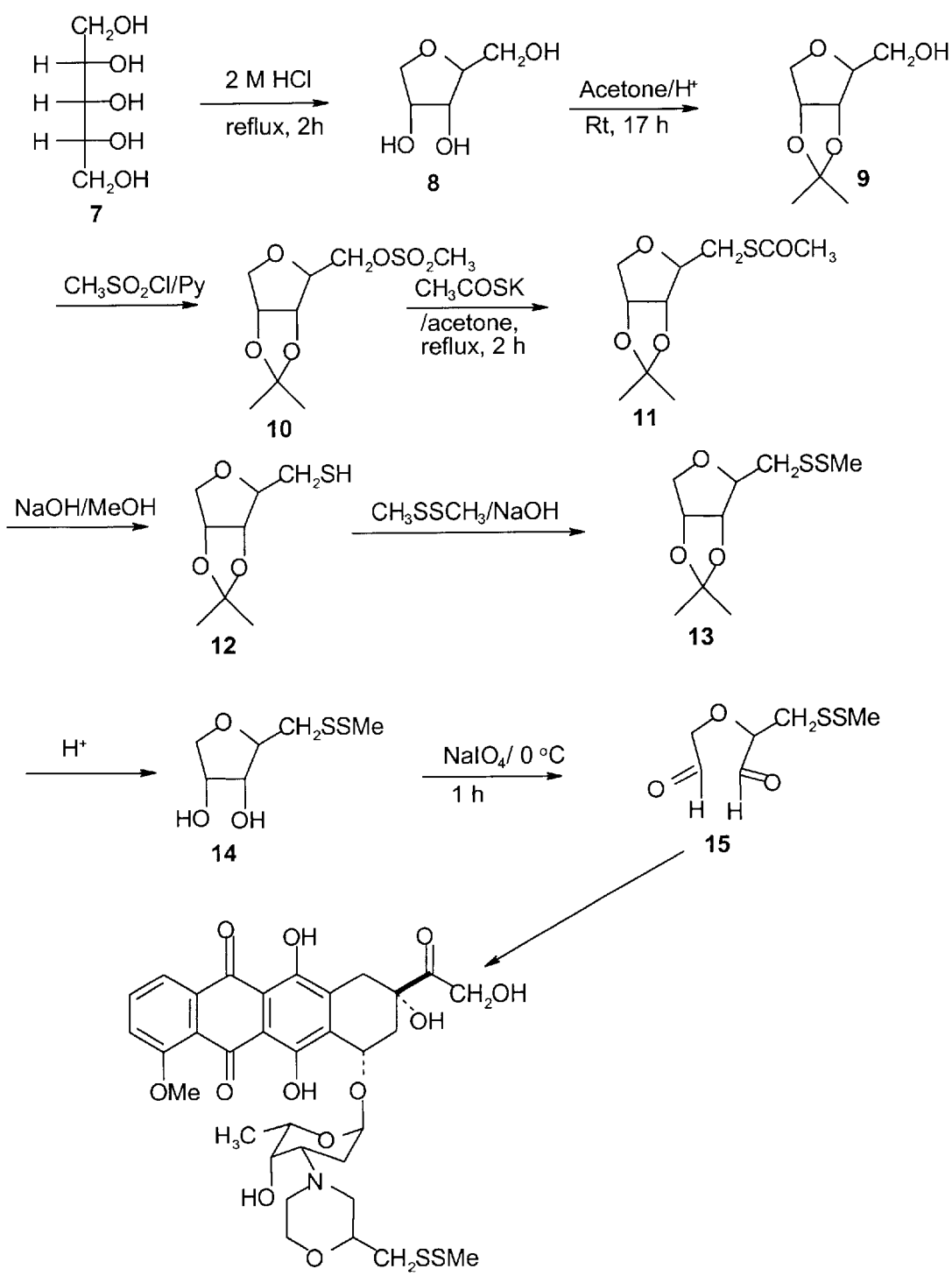
FIG. 3 shows the synthesis of methyldithiomorpholino doxorubicin from ribitol and doxorubicin.

The modified doxorubicins/daunorubicins can be synthesized according to known methods. The starting material for the synthesis is the commercially available doxorubicin or daunorubicin. First, an appropriate disulfide-containing anhydroribitol compound is synthesized. An example is provided in FIG. 3. The ribitol is then oxidized with sodium periodate, as described previously by E. M. Acton et al, supra. Reaction of the resulting dialdehyde with doxorubicin followed by reduction with sodium cyanoborohydride provides the disulfide-containing morpholino doxorubicin (FIG. 3). The disulfide or thiol-containing substituent can be introduced as an ether substituent at R' by conversion of the alcohol at R' into an ether by standard chemical methods. For example, the primary hydroxyl group of an appropriately protected anhydroribitol (such as protection of the diol by an isopropylidene group), is reacted with an excess of a dihalo compound, such as 1,3-dibromobutane, to give a halo ether. Displacement of the halogen with a thiol by reaction with potassium thioacetate, followed by treatment with mild base or hydroxylamine provides the thiol-containing ribitol. The thiol group can be converted into a methyl or pyridyl disulfide by reaction with methyl methanethiol sulfonate or dithiodipyridine respectively. This method is described in U.S. Pat. No. 5,146,064, which is expressly incorporated herein by reference. Removal of the isopropylidene protecting group with acid, followed by periodate oxidation, and reaction of the resulting dialdehyde with doxorubicin or daunorubicin will provide the desired disulfide-containing morpholino doxorubicin or daunorubicin.

When either R or R' is not a linking group, the substituent in that position can be varied until a compound of the desired toxicity is obtained. High toxicity is defined as having an $IC_{50}$ towards cultured cancer cells in the range of $1 \times 10^{-12}$ to $1 \times 10^{-9}$ M, upon a 72 hour exposure time. Representative examples of substituents are H, alkyl, and O-alkyl, as described above. One of ordinary skill in the art can determine the appropriate chemical moiety for R and R' using only routine experimentation.

For example methyl and methoxy substituents are expected to increase the cytotoxic potency, while a hydrogen is not expected to increase the potency as compared to the parent doxorubicin or daunorubicin. Typically a few representative modified doxorubicins or daunorubicins with substituents at the different positions will be initially prepared and evaluated for in vitro cytotoxicity.

Disulfide-containing and thiol-containing doxorubicin/daunorubicin drugs of the invention can be evaluated for their ability to suppress proliferation of various unwanted cell lines in vitro. For example, cell lines such as the human epidermoid carcinoma line KB, the human breast tumor line SKBR3, and the Burkitt's lymphoma line Namalwa can easily be used for the assessment of cytotoxicity of these compounds. Cells to be evaluated can be exposed to the compounds for 72 hours and the surviving fractions of cells measured in direct assays by known methods. $IC_{50}$ values can then be calculated from the results of the assays.

The effectiveness of the compounds of the invention as therapeutic agents depends on the careful selection of an appropriate cell binding agent. Cell binding agents may be of any kind presently known, or that become known and include peptides and non-peptides. Generally, these can be antibodies (especially monoclonal antibodies), lymphokines, hormones, growth factors, vitamins, nutrient-transport molecules (such as transferrin), or any other cell binding molecule or substance.

More specific examples of cell binding agents that can be used include:

fragments of antibodies such as sFv, Fab, Fab', and $F(ab')_2$ (Parham, 131 *J. Immunol.* 2895–2902 (1983); Spring et al, 113 *J. Immunol.* 470–478 (1974); Nisonoff et al, 89 *Arch. Biochem. Biophys.* 230–244 (1960));

interferons (e.g. α, β, γ);

lymphokines such as IL-2, IL-3, IL-4, IL-6;

hormones such as insulin, TRH (thyrotropin releasing hormones), MSH (melanocyte-stimulating hormone), steroid hormones, such as androgens and estrogens;

vitamins such as folic acid growth factors and colony-stimulating factors such as EGF, TGF-α, G-CSF, M-CSF and GM-CSF (Burgess, 5 *Immunology Today* 155–158 (1984)); and transferrin (O'Keefe et al, 260 *J. Biol Chem.* 932–937 (1985)).

Monoclonal antibody techniques allow for the production of extremely specific cell binding agents in the form of specific monoclonal antibodies. Particularly well known in the art are techniques for creating monoclonal antibodies produced by immunizing mice, rats, hamsters or any other mammal with the antigen of interest such as the intact target cell, antigens isolated from the target cell, whole virus, attenuated whole virus, and viral proteins such as viral coat proteins. Sensitized human cells can also be used. Another method of creating monoclonal antibodies is the use of phage libraries of sFv (single chain variable region), specifically human sFv. (See e.g., Griffiths et al, U.S. Pat. No. 5,885,793; McCafferty et al, WO 92/01047; Liming et al, WO 99/06587.)

Selection of the appropriate cell binding agent is a matter of choice that depends upon the particular cell population that is to be targeted, but in general monoclonal antibodies are preferred, if an appropriate one is available.

For example, the monoclonal antibody J5 is a murine $IgG_{2a}$ antibody that is specific for Common Acute Lymphoblastic Leukemia Antigen (CALLA) (Ritz et al, 283 *Nature* 583–585 (1980)) and can be used if the target cells express CALLA such as in the disease of acute lymphoblastic leukemia. Similarly, the monoclonal antibody anti-B4 is a murine $IgG_1$, that binds to the CD19 antigen on B cells (Nadler et al, 131 *J. Immunol.* 244–250 (1983)) and can be used if the target cells are B cells or diseased cells that express this antigen such as in non-Hodgkin's lymphoma or chronic lymphoblastic leukemia.

Additionally, GM-CSF, which binds to myeloid cells, can be used as a cell binding agent to diseased cells from acute myelogenous leukemia. IL-2, which binds to activated T-cells, can be used for prevention of transplant graft rejection, for therapy and prevention of graft-versus-host disease, and for treatment of acute T-cell leukemia. MSH, which binds to melanocytes, can be used for the treatment of melanoma. Folic acid, which targets the folate receptor expressed on ovarian and other cancers is also a suitable cell binding agent.

Cancers of the breast and testes can be successfully targeted with estrogen (or estrogen analogues) or androgen (or androgen analogues) respectively as cell binding agents.

Conjugates of the modified doxorubicins/daunorubicins of the invention and a cell binding agent can be formed using any techniques presently known or later developed. Numerous methods of conjugation are taught in U.S. Pat. No. 5,416,064. Morpholino ethers can be synthesized to yield a free amino group and then linked to an antibody or other cell binding agent via an acid labile linker or a photolabile linker. The morpholino (doxorubicin/daunorubicin) containing a free amino group can be condensed with a peptide and subsequently linked to a cell binding agent to produce a peptidase labile linker. Morpholino (doxorubicin/daunorubicin) containing a free hydroxyl group can be synthesized from doxorubicin/daunorubicin and ribitol and then succinylated and linked to a cell binding agent to produce a conjugate that can be cleaved by intracellular esterases to liberate free drug. Most preferably, the doxorubicin/daunorubicin ethers are treated to create a free or protected thiol group, and then the disulfide- or thiol-containing doxorubicins/daunorubicins are linked to the cell binding agent via disulfide bonds.

Representative conjugates of the invention are antibody-modified doxorubicin/daunorubicin, antibody fragment-modified doxorubicin/daunorubicin epidermal growth factor (EGF)-modified doxorubicin/daunorubicin, melanocyte stimulating hormone (MSH)-modified doxorubicin/daunorubicin, thyroid stimulating hormone (TSH)-modified doxorubicin/daunorubicin, estrogen-modified doxorubicin/daunorubicin, estrogen analogue-modified doxorubicin/daunorubicin, androgen-modified doxorubicin/daunorubicin, androgen analogue-modified doxorubicin/daunorubicin, and folate-modified doxorubicin/daunorubicin.

Modified doxorubicin/daunorubicin conjugates of antibodies, antibody fragments, protein or peptide hormones, protein or peptide growth factors and other proteins are made in the same way by known methods. For example, peptides and antibodies can be modified with cross linking reagents such as N-succinimidyl 3-(2-pyridyldithio) propionate, N-succinimidyl 4-(2-pyridyldithio)pentanoate (SPP), 4-succinimidyl-oxycarbonyl-α-methyl-α-(2-pyridyl dithio)-toluene (SMPT), N-succinimidyl-3-(2-pyridyldithio) butyrate (SDPB), 2-iminothiolane, or S-acetylsuccinic anhydride by known methods. See, Carlsson et al, 173 *Biochem. J.* 723–737 (1978); Blattler et al, 24 *Biochem.* 1517–1524 (1985); Lambert et al, 22 *Biochem.* 3913–3920 (1983); Klotz et al, 96 *Arch. Biochem. Biophys.* 605 (1962); and Liu et al, 18 *Biochem.* 690 (1979), Blakey and Thorpe, 1 *Antibody, Immunoconjugates & Radiopharmaceuticals,* 1–16 (1988), Worrell et al 1 *Anti-Cancer Drug Design* 179–184 (1986). The free or protected thiol-containing cell binding agent thus derived is then reacted with a disulfide- or thiol-containing doxorubicin/daunorubicin to produce conjugates. The conjugates can be purified by HPLC or by gel filtration.

Similarly, for example, estrogen and androgen cell binding agents such as estradiol and androstenediol can be esterified at the C-17 hydroxy group with an appropriate disulfide containing carboxylic acid using, for example, dicyclohexylcarbodiimide as a condensing agent. Examples of such carboxylic acids that can be employed are 3-(2-pyridyldithio)propanoic acid, 3-methyldithiopropanoic acid, 4-(2-pyridyldithio)pentanoic acid, and 3-phenyldithiopropanoic acid. Esterification of the C-17 hydroxy group can also be achieved by reaction with an appropriately protected thiol group containing carboxylic acid chloride such as 3-S-acetylpropanoyl chloride. Other methods of esterification can also be employed as described in the literature (Haslam, 36 *Tetrahedron* 2409–2433 (1980)). The protected or free thiol-containing androgen or estrogen can then be reacted with a disulfide- or thiol-containing doxorubicin/daunorubicin to produce conjugates. The conjugates can be purified by column chromatography on silica gel or by HPLC. Folic acid can be condensed with a suitable hydrazide such as 4-(2-pyridyldithio)pentanoic acid hydrazide in the presence of a condensing agent such as dicyclohexyl carbodiimide to give a hydrazone containing an active disulfide. The disulfide-containing folate can then be reacted with a thiol-containing doxorubicin/daunorubicin to produce a conjugate that can be purified by column chromatography over silica gel or by HPLC.

Preferably monoclonal antibody- or cell binding agent-doxorubicin/daunorubicin conjugates are those that are joined via a disulfide bond, as discussed above, that are capable of delivering doxorubicin/daunorubicin molecules. Such cell binding conjugates are prepared by known methods such as by modifying monoclonal antibodies with succinimidyl pyridyl-dithiopropionate (SPDP) (Carlsson et al, 173 *Biochem. J.* 723–737 (1978)). The resulting thiopyridyl group is then displaced by treatment with thiol-containing doxorubicins/daunorubicins to produce disulfide linked conjugates. Alternatively, in the case of the aryldithio-doxorubicins/daunorubicins, the formation of the cell binding conjugate is effected by direct displacement of the aryl-thiol of the doxorubicin/daunorubicin with sulfhydryl groups previously introduced into antibody molecules. Conjugates containing 1 to 10 doxorubicin/daunorubicin drugs linked via a disulfide bridge are readily prepared by either method.

More specifically, a solution of the dithiopyridyl modified antibody at a concentration of 1 mg/ml in 0.1 M potassium phosphate buffer, at pH 6.5 containing 1 mM EDTA is treated with the thiol-containing doxorubicin/daunorubicin (1.25 molar equivalent/dithiopyridyl group). The release of thiopyridine from the modified antibody is monitored spectrophotometrically at 343 nm and is complete in about 20 hours. The antibody-modified doxorubicin/daunorubicin conjugate is purified and freed of unreacted drug and other low molecular weight material by gel filtration through a column of Sephadex G-25 or Sephacryl S300. The number of modified doxorubicin/daunorubicin moieties bound per antibody molecule can be determined by measuring the ratio of the absorbance at 280 nm and 490 nm. An average of 1–10 modified doxorubicin/daunorubicin molecules/antibody molecule can be linked via disulfide bonds by this method.

Antibody-modified doxorubicin/daunorubicin conjugates with non-cleavable links can also be prepared. The antibody can be modified with crosslinking reagents such as succinimidyl 4-(maleimidomethyl)cyclohexane-1-carboxylate (SMCC), sulfo-SMCC, m-maleimidobenzoyl-N-hydroxysuccinimide ester (MBS), sulfo-MBS or succinimidyl-iodoacetate, as described in the literature, to introduce 1–10 reactive groups. See, Yoshitake et al, 101 *Eur. J. Biochem.* 395–399 (1979); Hashida et al, *J. Applied Biochem.* 56–63 (1984); and Liu et al, 18 *Biochem.* 690–697 (1979). The modified antibody is then reacted with the thiol-containing doxorubicin/daunorubicin derivative to produce a conjugate. The conjugate can be purified by gel filtration through a Sephadex G-25 column.

The modified antibodies are treated with the thiol-containing doxorubicins/daunorubicins (1.25 molar equivalent/maleimido group). The mixtures are incubated overnight at about 4° C. The antibody-modified doxorubicin/daunorubicin conjugates are purified by gel filtration through a Sephadex G-25 column. Typically, an average of 1 to 10 modified doxorubicin/daunorubicin molecules per antibody are linked.

A preferred method is to modify antibodies with succinimidyl-4-(maleimidomethyl)-cyclohexane-1-carboxylate (SMCC) to introduce maleimido groups followed by reaction of the modified antibody with the thiol-containing doxorubicins/daunorubicins to give a thioether linked conjugate. Again conjugates with 1 to 10 drug molecules per antibody molecule result.

Cytotoxicity of the modified doxorubicins/daunorubicins and their antibody conjugates to non-adherent cell lines such as Namalwa and HL-60 can be measured by back-extrapolation of cell proliferation curves as described in Goldmacher et al, 135 *J. Immunol.* 3648–3651 (1985). Cytotoxicity of these compounds to adherent cell lines such as SKBR3 and KB can be determined by clonogenic assays as described in Goldmacher et al, 102 *J. Cell Biol.* 1312–1319 (1986).

The present invention also provides a therapeutic composition comprising:

(A) an effective amount of one or more modified doxorubicins/daunorubicins linked to a cell binding agent, and (B) a pharmaceutically acceptable carrier.

Similarly, the present invention provides a method for killing selected cell populations comprising contacting target cells or tissue containing target cells with an effective amount of a cytotoxic agent comprising one or more modified doxorubicins/daunorubicins linked to a cell binding agent.

The cytotoxic agent is prepared as described above.

Conjugates can be evaluated for in vitro potency and specificity by methods previously described—see R. V. J. Chari et al, 55 *Cancer Res.* 4079–4084 (1995). Anti-tumor activity can be evaluated in human tumor xenograft models in mice by methods previously described (see C. Liu et al, 93 *Proc. Natl. Acad. Sci.* 8618–8623 (1996)).

Suitable pharmaceutically acceptable carriers are well known and can be determined by those of ordinary skill in the art as the clinical situation warrants. As used herein, carriers include diluents and excipients.

Examples of suitable carriers, diluents and/or excipients include: (1) Dulbecco's phosphate buffered saline, pH about 7.4, containing or not containing about 1 mg/ml to 25 mg/ml human serum albumin, (2) 0.9% saline (0.9% w/v NaCl), and (3) 5% (w/v) dextrose; and may also contain an antioxidant such as tryptamine and a stabilizing agent such as Tween 20.

The method for killing selected cell populations can be practiced in vitro, in vivo, or ex vivo.

Examples of in vitro uses include treatments of autologous bone marrow prior to their transplant into the same patient in order to kill diseased or malignant cells: treatments of bone marrow prior to their transplantation in order to kill competent T cells and prevent graft-versus-host-disease (GVHD); treatments of cell cultures in order to kill all cells except for desired variants that do not express the target antigen; or to kill variants that express undesired antigen.

The conditions of non-clinical in vitro use are readily determined by one of ordinary skill in the art.

Examples of clinical ex vivo use are to remove tumor cells or lymphoid cells from bone marrow prior to autologous transplantation in cancer treatment or in treatment of autoimmune disease, or to remove T cells and other lymphoid cells from autologous or allogeneic bone marrow or tissue prior to transplant in order to prevent GVHD. Treatment can be carried out as follows. Bone marrow is harvested from the patient or other individual and then incubated in medium containing serum to which is added the cytotoxic agent of the invention. Concentrations range from about 10 $\mu$M to 1 pM, for about 30 minutes to about 48 hours at about 37° C. The exact conditions of concentration and time of incubation, i.e., the dose, are readily determined by one of ordinary skill in is the art. After incubation the bone marrow cells are washed with medium containing serum and returned to the patient by i.v. infusion according to known methods. In circumstances where the patient receives other treatment such as a course of ablative chemotherapy or total-body irradiation between the time of harvest of the marrow and reinfusion of the treated cells, the treated marrow cells are stored frozen in liquid nitrogen using standard medical equipment.

For clinical in vivo use, the cytotoxic agent of the invention will be supplied as solutions that are tested for sterility and for endotoxin levels. Examples of suitable protocols of conjugate administration are as follows. Conjugates are given weekly for 4 weeks as an i.v. bolus each week. Bolus doses are given in 50 to 100 ml of normal saline to which 5 to 10 ml of human serum albumin can be added. Dosages will be 10 μg to 2000 mg per administration, i.v. (range of 100 ng to 20 mg/kg per day). After four weeks of treatment, the patient can continue to receive treatment on a weekly basis. Specific clinical protocols with regard to route of administration, excipients, diluents, dosages, times, etc., can be determined by one of ordinary skill in the art as the clinical situation warrants.

Examples of medical conditions that can be treated according to the in vivo or ex vivo methods of killing selected cell populations include malignancy of any type including, for example, cancer of the lung, breast, colon, prostate, kidney, pancreas, ovary, and lymphatic organs; autoimmune diseases, such as systemic lupus, rheumatoid arthritis, and multiple sclerosis; graft rejections, such as renal transplant rejection, liver transplant rejection, lung transplant rejection, cardiac transplant rejection, and bone marrow transplant rejection; graft versus host disease; viral infections, such as mV infection, HIV infection, AIDS, etc.; and parasite infections, such as giardiasis, amoebiasis, schistosomiasis, and others as determined by one of ordinary skill in the art.

EXAMPLES

The invention will now be illustrated by reference to non-limiting examples. Unless otherwise stated, all percents, ratios, parts, etc. are by weight.

Example 1

Synthesis of Disulfide-containing Morpholinodoxorubicin

The synthesis of a representative disulfide-containing morpholinodoxorubicin is shown schematically in FIG. 3. Ribitol (7), which is commercially available, is converted into anhydroribitol 8 by acid catalyzed dehydration. Protection of the diol in 8 by conversion into the isopropylidene 9, followed by reaction of the free hydroxyl group with methanesulfonylchloride gave the mesylate 10. Reaction of 10 with potassium thioacetate afforded 11. Hydrolysis of the thioester with base, followed by disulfide exchange of the thiol in 12 with methyldisulfide gave the methyldithio compound 13. The isopropylidene protecting group was then removed by acid hydrolysis to give 5-methyldithio-(1,4-anhydro)ribitol (14). Periodate oxidation of the diol gave the dialdehyde 15, which was treated in situ with doxorubicin in the presence of sodium cyanoborohydride to give methydithiomorpholinodoxorubicin 16.

Example 2

In Vitro Cytotoxicity Assays

The sulfide, disulfide, and sulfhydryl-containing doxorubicin/daunorubicin drugs of the invention can be evaluated for their ability to suppress proliferation of various human tumor cell lines in vitro. Two adherent cell lines KB (human epidermoid carcinoma) and SKBR3 (human breast tumor) and the non-adherent cell line, Namalwa (Burkitt's lymphoma) are used for the assessment of cytotoxicity of these compounds. Cells are exposed to the compounds for 72 hours and the surviving fractions of cells are measured in direct assays. (KB and SKBR3 are assayed for plating efficiency (Goldmacher et al, 102 *J. Cell. Biol.* 1312–1319 (1986) and Namalwa are assayed by growth back extrapolation (Goldmacher et al, 135 *J. Immunol.* 3648–3651 (1985)). $IC_{50}$ values are then calculated from this data.

Example 3

Conjugation to Antibodies

Conjugation of Thiol-Containing Doxorubicins/ Daunorubicins to Antibodies via Disulfide Links The conjugation of thiol-containing doxorubicins/ daunorubicins to antibodies via disulfide links is performed in two steps. In the first step dithiopyridyl groups are introduced into antibodies using succinimidyl pyridyldithiopropionate (SPDP) as described by Carlsson et al. The thiopyridyl groups are then displaced by reaction with the thiol-containing doxorubicin/daunorubicin to produce a conjugate.

Preparation of Antibody-SS-Doxorubicin/Daunorubicin Conjugates. Antibodies anti-B4, anti-T9 and N901 are modified with SPDP or SPP as described in the literature. Between 1 to 10 dithiopyridyl groups are introduced on the average per antibody molecule.

A solution of the dithiopyridyl modified antibody at a concentration of 1 mg/ml in 0.1 M potassium phosphate buffer pH 6.5 containing 1 mM EDTA at 25° C. is treated with a thiol-containing doxorubicin/daunorubicin (1.25 molar equivalent/dithiopyridyl group). The release of thiopyridine from the modified antibody is monitored spectrophotometrically at 343 nm and is found to be complete in about 20 hours. The antibody-modified doxorubicin/ daunorubicin conjugate is purified and freed of unreacted drug and other low molecular weight material by gel filtration through a column of Sephadex G-25. The number of modified doxorubicin/daunorubicin molecules bound per antibody molecule is determined by measuring the ratio between the absorbances at 280 nm and 490 nm. An average of 1–10 modified doxorubicin/daunorubicin molecules per antibody molecule can be linked via disulfide bonds by this method.

Conjugation of Thiol-Containing Modified Doxorubicin/ Daunorubicin to Antibodies via a Noncleavable Thioether Link: The conjugation of a thiol-containing doxorubicin/ daunorubicin is performed in two steps. The antibody is first reacted with succinimidyl maleimidomethylcyclohexane carboxylate (SMCC) to introduce maleimido groups. The modified antibody is then reacted with the thiol-containing doxorubicin/daunorubicin forming thioether links.

Preparation of Antibody-Modified Doxorubicin/ Daunorubicin Conjugates (Non-Cleavable). Antibodies, anti-B4, anti-T9, and N901 are modified with SMCC as described in the literature.

The modified antibodies are treated with thiol-containing doxorubicin/daunorubicin (1.25 molar equivalent/ maleimido group). The mixtures are incubated overnight at 4° C. The antibody-modified doxorubicin/daunorubicin conjugates are purified as described above. Typically, an average of 1–10 modified doxorubicin/daunorubicin molecules per antibody molecule are linked.

Example 4

Other Methods of Linking Doxorubicins/ Daunorubicins

Acid Labile Linkers

Morpholino doxorubicins/daunorubicins containing an amino substituent can be synthesized by standard methods described in the chemical literature. This amino group containing doxorubicins/daunorubicins can be linked to antibodies and other cell binding agents via an acid labile linker as previously described (Blättler et al, 24 *Biochemistry*, 1517–1524 (1985), U.S. Pat. Nos. 4,542,225, 4,569,789 and 4,764,368).

Photolabile Linker

The amino group-containing doxorubicin/daunorubicin derivative described above can be linked to cell binding agents via a photolabile linker as previously described. (Senter et al, 42 *Photochemistry and Photobiology*, 231–237 (1985), U.S. Pat. No. 4,625,014).

Peptidase Labile Linker

The amino group-containing doxorubicin/daunorubicin described above can also be linked to cell binding agents via peptide spacer linkers. It has been previously shown that short peptide spacers between drugs and macromolecular protein carriers are stable in serum but are readily hydrolyzed by intracellular lysosomal peptidases (Trouet et al, 79 *Proc. Nat'l. Acad. Sci.*, 626–629 (1982)). The amino group containing doxorubicin/daunorubicin can be condensed with peptides such as Ala-Leu, Leu-Ala-Leu and Ala-Leu-Ala-Leu using condensing agents such as 1-[3-(dimethylamino)propyl]-3-ethyl carbodiimide-HCl to give a peptide derivative of doxorubicin/daunorubicin which can then be linked to cell binding agents.

Esterase Labile Linker

Morpholino Doxorubicins/daunorubicins can be esterified by reaction of the hydroxyl group with succinic anhydride and then linked to a cell binding agent to produce a conjugate that can be cleaved by intracellular esterases to liberate free drug. (For examples see: Aboud-Pirak et al, 38 *Biochem. Pharmacol.* 641–648 (1989), Laguzza et al, 32 *J. Med. Chem.* 549–555 (1989)).

Example 5

Cell Cultures and In Vitro Cytotoxicity Assays

Cells of the human promyelocytic leukemia cell line, HL-60 (ATCC CCL 240) and the Burkitt's lymphoma cell line Namalwa (ATCC CRL 1432) are grown as suspension cultures in RPMI-1640 medium supplemented with 10% fetal calf serum and 2 mM L-glutamine. All other cell lines described below are grown as adherent cultures. Human epidermoid carcinoma cell line, KB (ATCC CCL 17), human renal carcinoma cell line A498 (ATCC HTB 44), human colon adenocarcinoma cell lines SW620 (ATCC CCL 227) and HT-29 (ATCC HTB 38) are grown in RPMI-1640 medium supplemented with 10% fetal calf serum and 2 mM L-glutamine. Human breast carcinoma SKBR3 cells (ATCC HTB 30) are grown in DMEM supplemented with 15% fetal calf serum containing 2 mM glutamine and the human ovarian adenocarcinoma cell line OVCAR3 (ATCC HTB 161) is grown in RPMI-1640 medium supplemented with 10% fetal calf serum containing 10 µg/ml insulin and 2 mM L-glutamine.

Three different antibodies are used for conjugation via disulfide links to thiol-containing doxorubicins/daunorubicins. Conjugates are prepared with the antibodies anti-B4, which is against the B cell antigen CD19; anti-T9 (5E9) which is an anti-human transferrin receptor antibody, and N901, which is an anti-human small cell lung cancer antibody.

Cytotoxicity assays are performed in the respective media described above. The cytotoxicity of the modified doxorubicins/daunorubicins and their antibody conjugates to HL-60 and Namalwa cells are measured by back-extrapolation of cell proliferation curves. Cytotoxicity of these compounds to the rest of the cell lines is determined by clonogenic assay as previously described.

The conjugates are assessed for in vitro cytotoxicity and the $IC_{50}$ values for cell lines are determined.

Example 6

Determination of Specific Affinity of Antibody-Modified Doxorubicin/Daunorubicin Conjugates The specific affinities of disulfide linked N901-modified doxorubicin/daunorubicin conjugates are analyzed by competition binding assays. The competition of binding of FITC-labeled antibody to NCI N417 and NCI H69 cells by unlabeled antibody and antibody-modified doxorubicin/daunorubicin conjugates are determined by direct immunofluorescence on a Becton-Dickinson FACS. The two cell lines are grown as adherent cells in tissue culture grade flasks containing Dulbecco's modified minimum essential medium with 15% fetal bovine calf serum. The cells are then trypsinized and incubated in suspension, at 37° C., for 30 minutes in the same medium in non-tissue culture grade flasks to prevent adherence of cells to the plastic. The cells are then transferred to wells of 96 well plates and resuspended in minimum essential medium containing 25% pooled human serum. Cell suspensions (0.2 ml suspension containing 100,000 cells/well) are incubated with 6 nM FITC-labeled antibody N901, at varied concentrations of unlabeled antibody or modified doxorubicin/daunorubicin conjugates for 1 hour at 0° C. The cells are then washed once with buffer and fixed with 1% formaldehyde in phosphate buffered saline. Mean cell fluorescence is measured on a FACS.

Example 7

In Vivo Clearance Studies and Pharmacokinetics

Blood clearances of a typical $^{125}$I-labelled murine $IgG_1$ antibody and of its corresponding $^{125}$I-labelled modified doxorubicin/daunorubicin conjugate, containing an average of 4 drug molecules/antibody molecule, are determined in female CD-1 mice. The antibody and the modified doxorubicin/daunorubicin conjugates are radio-iodinated by the method of Bolton and Hunter (133 *Biochem. J.* 529–539 (1973)). The antibody and conjugates are injected separately i.v. into the tail vein. Heparinized blood samples are collected from the retroorbital venus plexus at the indicated times and measured for radioactivity content.

While the invention has been described in detail and with reference to specific embodiments thereof, it will be apparent to one of ordinary skill in the art that various changes and modifications can be made therein without departing from the spirit and scope of the invention.

What is claimed is:

1. A compound represented by formula (I):

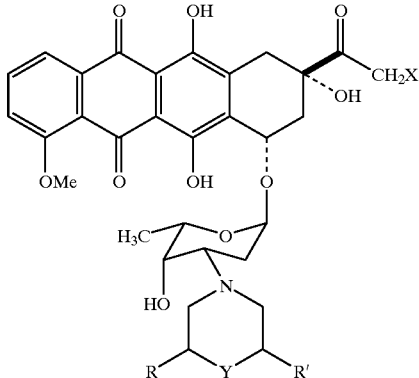

wherein,
- X is H or OH;
- Y is O or $NR_2$, wherein $R_2$ is linear or branched alkyl having 1 to 5 carbon atoms;
- R is a linking group, H, or linear or branched alkyl having 1 to 5 carbon atoms; and
- R' is a linking group, H, or —$OR_1$, wherein $R_1$ is linear or branched alkyl having 1 to 5 carbon atoms;
- provided that one of R and R' is a linking group, but R and R' are not linking groups at the same time.

2. The compound of claim 1, wherein X is H.
3. The compound of claim 1, wherein X is OH.
4. The compound of claim 1, wherein the linking group is a thiol- or disulfide-containing moiety.
5. The compound of claim 1, wherein the linking group is —$(CH_2)_nSZ$, —$O(CH_2)_nSZ$, —$(CH_2)_nCH(CH_3)SZ$, —$O(CH_2)_nCH(CH_3)SZ$, —$(CH_2)_nC(CH_3)_2SZ$, or —$O(CH_2)_nC(CH_3)_2SZ$, wherein
- Z is H or $SR_3$, wherein $R_3$ is linear, branched, or cyclic alkyl having from 1 to 10 carbon atoms, or simple or substituted aryl having from 1 to 10 carbon atoms, or heterocyclic, and
- n is an integer of 1 to 10.

6. The compound of claim 1, wherein $NR_2$ is $NCH_3$.
7. The compound of claim 1, wherein R' is —$OCH_3$.
8. A cytotoxic agent comprising one or more compounds covalently bonded to a cell binding agent through a linking group, wherein at least one of said compounds is a compound represented by formula (I):

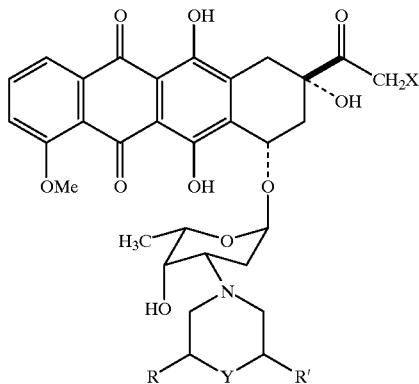

wherein,
- X is H or OH;
- Y is O or $NR_2$, wherein $R_2$ is linear or branched alkyl having 1 to 5 carbon atoms;
- R is a linking group or —$CH_3$; and
- R' is a linking group, —$OCH_3$, or H;
- provided that one of R and R' is a linking group, but R and R' are not linking groups at the same time.

9. The cytotoxic agent of claim 8, wherein X is H.
10. The cytotoxic agent of claim 8, wherein X is OH.
11. The cytotoxic agent of claim 8, wherein the linking group is a thiol- or disulfide-containing moiety.
12. The cytotoxic agent of claim 8, wherein the linking group is —$(CH_2)_nSZ$, —$O(CH_2)_nSZ$, —$(CH_2)_nCH(CH_3)SZ$, —$O(CH_2)_nCH(CH_3)SZ$, —$(CH_2)_nC(CH_3)_2SZ$, or —$O(CH_2)_nC(CH_3)_2SZ$, wherein
- Z is H or $SR_3$, wherein $R_3$ is linear, branched, or cyclic alkyl having from 1 to 10 carbon atoms, or simple or substituted aryl having from 1 to 10 carbon atoms, or heterocyclic, and
- n is an integer of 1 to 10.

13. The cytotoxic agent of claim 8, wherein $NR_2$ is $NCH_3$.
14. The cytotoxic agent of claim 8, wherein R' is —$OCH_3$.
15. A therapeutic composition comprising:
(A) a therapeutically effective amount of the cytotoxic agent of claim 8; and
(B) a pharmaceutically acceptable carrier.
16. A method of killing selected cell populations comprising contacting target cells or tissue containing target cells with an effective amount of the cytotoxic agent of claim 8.

* * * * *